(12) United States Patent
Schardt et al.

(10) Patent No.: US 8,549,904 B2
(45) Date of Patent: *Oct. 8, 2013

(54) FLUIDIC VOLUME DISPENSE VERIFICATION TOOL

(75) Inventors: Phillip Schardt, Boulevard, CA (US); Chris Langley, San Diego, CA (US); James Light, San Diego, CA (US)

(73) Assignee: Gamida for Life, B.V., Rotterdam (NL)

(*) Notice: Subject to any disclaimer, the term of this patent is extended or adjusted under 35 U.S.C. 154(b) by 274 days.

This patent is subject to a terminal disclaimer.

(21) Appl. No.: 12/946,951

(22) Filed: Nov. 16, 2010

(65) Prior Publication Data

US 2011/0056287 A1    Mar. 10, 2011

Related U.S. Application Data

(63) Continuation of application No. 11/948,627, filed on Nov. 30, 2007, now Pat. No. 7,861,581.

(60) Provisional application No. 60/872,252, filed on Dec. 1, 2006.

(51) Int. Cl.
*G01F 17/00* (2006.01)

(52) U.S. Cl.
USPC ............................................. 73/149

(58) Field of Classification Search
USPC .................................................. 73/149
See application file for complete search history.

(56) References Cited

U.S. PATENT DOCUMENTS 1,607,706 A    11/1926 Toulmin, Jr.
2,329,412 A *  9/1943 Nelson .................... 73/290 R
4,756,884 A    7/1988 Hillman et al.
4,959,324 A    9/1990 Ramel et al.
5,212,979 A    5/1993 Albrodt et al.
5,234,813 A    8/1993 McGeehan et al.
5,693,318 A    12/1997 Burke et al.
6,097,831 A    8/2000 Wieck et al.
6,207,369 B1   3/2001 Wohlstadter et al.
6,983,636 B2   1/2006 Johnson et al.
7,614,298 B2 * 11/2009 Bohmer ........................ 73/149
2003/0059794 A1  3/2003 Vogels et al.

(Continued)

FOREIGN PATENT DOCUMENTS

WO    WO 99/36176     7/1999
WO    WO 2008/070548  6/2008

OTHER PUBLICATIONS

Feb. 16, 2010 Office Action in connection with U.S. Appl. No. 11/948,627.
Aug. 19, 2010 Notice of Allowability and Notice of Allowance in connection with U.S. Appl. No. 11/948,627.
Sep. 14, 2010 Supplemental Notice of Allowability in connection with U.S. Appl. No. 11/948,627.

(Continued)

*Primary Examiner* — Peter Macchiarolo
*Assistant Examiner* — Alex Devito
(74) *Attorney, Agent, or Firm* — John P. White; Cooper & Dunham LLP (57) ABSTRACT

Disclosed herein is a device for measuring fluid dispense volumes including one or more wells adapted to receive a fluid; a tube having an internal passageway fluidly coupled to the one or more wells, wherein fluid in the wells passes into the internal passageway via capillary action to form a fluid column having a meniscus spaced from the wells; and a scale coupled to the tube, the scale calibrated to provide an indication of the volume of the fluid based upon the location of the meniscus in the fluid passageway.

14 Claims, 9 Drawing Sheets

(56) References Cited

U.S. PATENT DOCUMENTS

2004/0069205 A1    4/2004    Lee et al.
2004/0129678 A1    7/2004    Crowley et al.
2005/0285060 A1    12/2005    Haga et al.
2008/0233009 A1    9/2008    Schardt et al.

OTHER PUBLICATIONS

Nov. 1, 2010 Response to Rule 312 Communication in connection with U.S. Appl. No. 11/948,627.

* cited by examiner

FLUIDIC VOLUME DISPENSE VERIFICATION TOOL

REFERENCE TO PRIORITY DOCUMENT

This application is a continuation of prior U.S. application Ser. No. 11/948,627 filed Nov. 30, 2007 now U.S. Pat. No. 7,861,581, which claims the benefit of prior U.S. Provisional Application Serial No. 60/872,252 filed Dec. 1, 2006. Benefit of the aforementioned prior filing dates is hereby claimed and the disclosure of the aforementioned prior applications is hereby incorporated by reference in its entirety.

BACKGROUND

Disclosed herein are devices and methods for measuring reagent volumes and determining the accuracy of liquid dispensers used in biochemical and biomedical assays. More particularly, disclosed herein are devices used with robotic equipment in the processing of microtiter-plate based assays. The devices and methods permit verification of the accuracy of the dispensing portion of diagnostic instruments in the analysis of samples.

The development of microtiter-plate methods allows the processing of a large number of samples simultaneously. Several laboratory and robotic systems have been developed for the purpose of processing microtiter plates. These devices are designed to increase laboratory throughput and are generally preferred over non-automated processes. Automated systems are more efficient and easier to control with less chance for random procedural errors. Automated systems generate homogeneous assays and have helped to eliminate error-prone washing and transferring steps. Automated systems generally provide for the accurate and precise delivery of assay reagents and other necessary fluids to individual reaction vessels Automation techniques vary from simple semi-automated liquid handling systems to fully integrated automated systems that include multiple robot arms and pipetting stations. Although automated systems have improved quality and reproducibility of fluid transfer, periodic calibration and quality assurance determinations are required. The relatively small size of the wells on the microtiter plate requires the precise delivery of a minute amount of sample. Inaccuracies in the delivery of samples can lead to erroneous results. In order to safeguard the accuracy of the results, the volume delivered by the automated devices must be routinely verified. Assuring the accuracy of biochemical assays is a critical concern for those in the medical diagnostic arts.

Two common techniques for checking the precision and accuracy of fluid dispensers are gravimetric and spectrophotometric techniques. The gravimetric technique is based on the weight of a pure sample of water dispensed by the device. The water is weighed using a balance calibrated with NIST-traceable weights. The actual dispensed volume is calculated from the measured weight and the density, taking into account temperature and evaporation rate. The proper type of equipment and operating environment which are needed to make gravimetric verification of automated pipetting devices are usually not available in a clinical laboratory and requires a visit by a field service technician to perform the diagnostic tests on site. Precision balances are expensive and difficult to use in the field service environment. They are sensitive to various environmental influences such as proximity to air conditioning vents, vibration and leveling. Precision balances also require careful set-up and regular calibration to ensure proper function. Thus, the skill level and time required to conduct these measurements are very high which makes gravimetric verification impractical in a clinical laboratory.

The spectrophotometric technique of volume verification employs a solution containing a known concentration of a high-colored chromagen. Aliquots of the sample solution are dispensed into a known volume of diluent and the absorbance measured. The actual dispensed volume is then calculated from the absorbance, the light path, the extinction coefficient and the diluent volume. In reality the concentration of the colorimetric reagent, cannot be precisely controlled. Therefore, verification techniques that calculate volume directly from the absorbance measured are often inaccurate. Furthermore, this method of volume verification is a manual procedure that is not performed in coordination with an automated workstation. The method requires additional solutions and is time consuming and prone to human error.

SUMMARY

Disclosed herein are devices and methods of use to verify the accuracy of fluid dispense volumes based upon capillary forces. The device and methods are highly accurate, easy to use, portable and universally designed for use with automated dispensing workstations.

Disclosed herein is a device for measuring fluid dispense volumes including one or more wells adapted to receive a fluid; a tube having an internal passageway fluidly coupled to the one or more wells, wherein fluid in the wells passes into the internal passageway via capillary action to form a fluid column having a meniscus spaced from the wells; and a scale coupled to the tube, the scale calibrated to provide an indication of the volume of the fluid based upon the location of the meniscus in the fluid passageway.

Other features and advantages should be apparent from the following description of various embodiments, which illustrate, by way of example, the principles of the disclosed device.

DETAILED DESCRIPTION

Disclosed is a measuring device that is adapted to verify the accuracy of fluid dispense volumes based upon capillary forces. The device includes a well that receives a volume of fluid. The well is fluidly coupled to a capillary tube having a graduated scale. The fluid moves from the well into the capillary tube pursuant to capillary action. As described in detail below, the distance the fluid travels into the capillary tube is used as a measure of the volume of the fluid that was received into the well. The graduated scale on the capillary tube can be calibrated to provide an indication as to the volume of fluid that was received into the well.

In an exemplary embodiment described herein, the device is used in combination with an automated workstation that transfers selected volumes of liquid (reagents, diluents and samples) to microtiter plate wells for transfer of sample to and from microtiter plates. Pursuant to such use, the device is described herein as being sized and shaped to interact with standard microtiter plates. However, it should be appreciated that the measuring device can be sized and shaped in other manners and is not limited to the particular embodiment described herein.

Figure 1:
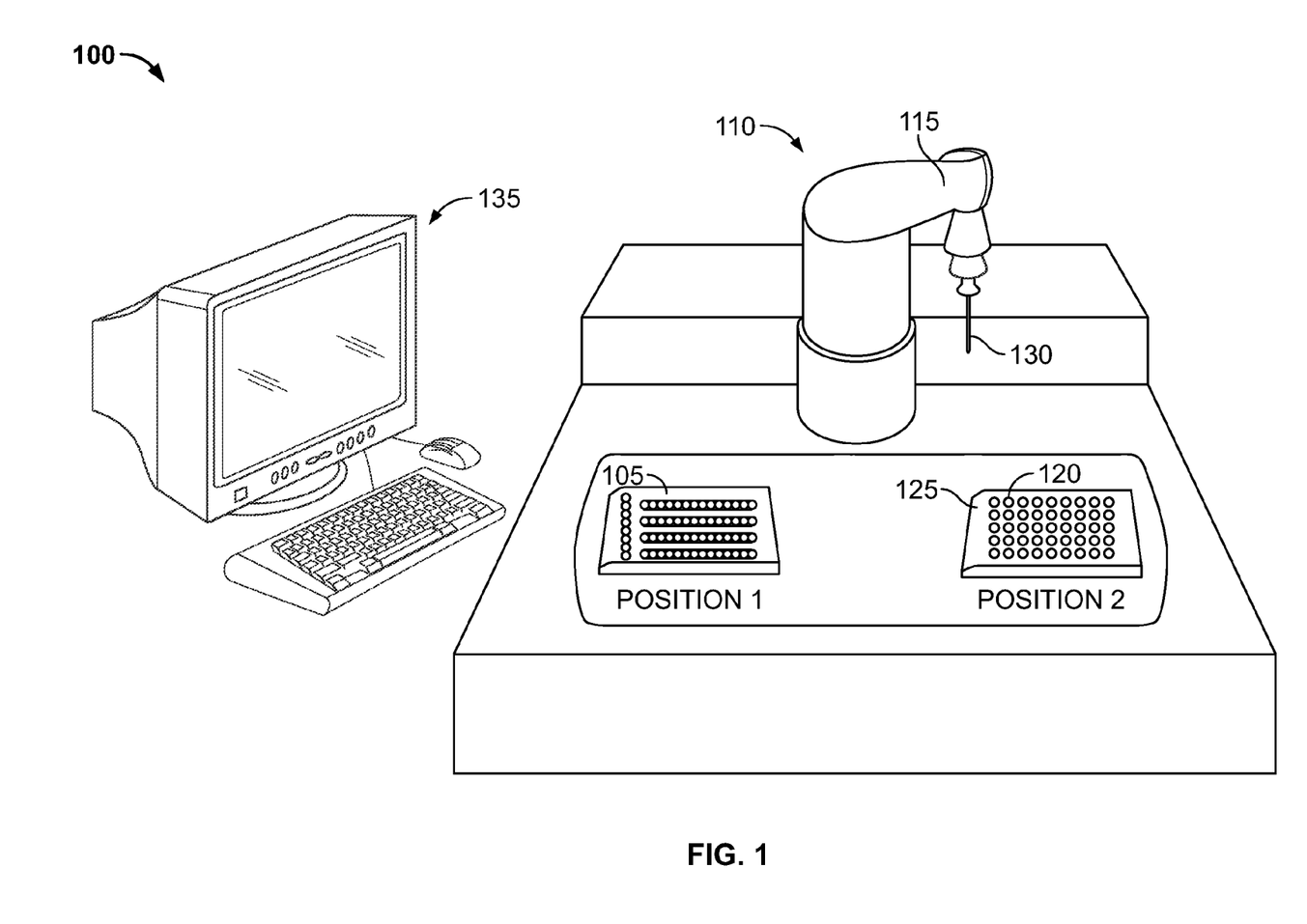
FIG. 1 shows a pictorial view of an exemplary volume dispense verification device used in coordination with an automated workstation having a robotic arm.

FIG. 1 shows an exemplary embodiment of a measuring device 105 in use with an automated workstation 100. The automated workstation 100 can be, for example, the NanoChip® 400 System (NC400 Nanogen, Inc., San Diego, Calif.) The automated workstation 100 includes a robotic type instrument 110 in which a robotic arm 115 transfers selected volumes of liquid (reagents, diluents and samples) to microtiter plate wells 120 for transfer of sample to and from microtiter plates 125. Standard microtiter plate wells 120 are arranged in rows and columns, for example an 8×12 assay of wells 120. The samples to be processed are held in a sample carrier location, labeled "Position 1" and "Position 2" in the figure. Dispensing pipette(s) 130 mounted on the robotic arm 115 can withdraw samples from the sample locations and transfer them to microtiter plate wells 120 of microtiter plates 125. Additional accessories can be incorporated into the automated workstation such as a computer 135 that runs software known in the art to control the automated workstation 100. Reagent and diluent reservoirs can also be incorporated into the automated workstation 100. It should be appreciated that the use of the device 105 with the automated workstation 100 is exemplary and that the device 105 can be used in other settings and environments. In addition, the automated workstation 100 is not limited to the particular configuration shown in FIG. 1.

The pictorial view of FIG. 1 shows the device 105 positioned within a sample carrier shown as position 1 of the automated workstation 100. In one embodiment, the device 105 is dimensioned to coincide with the dimensions of microtiter assay plates known in the art, for example Nunc™ microtiter plates. This provides the device 105 with a universal configuration that allows for the device 105 to be used with a variety of microtiter plate machines, including automated workstations, regardless of brand or type of machine. The device 105 can also be dimensioned according to other types and sizes of microtiter plates or according to other dimensions.

Figure 2A:
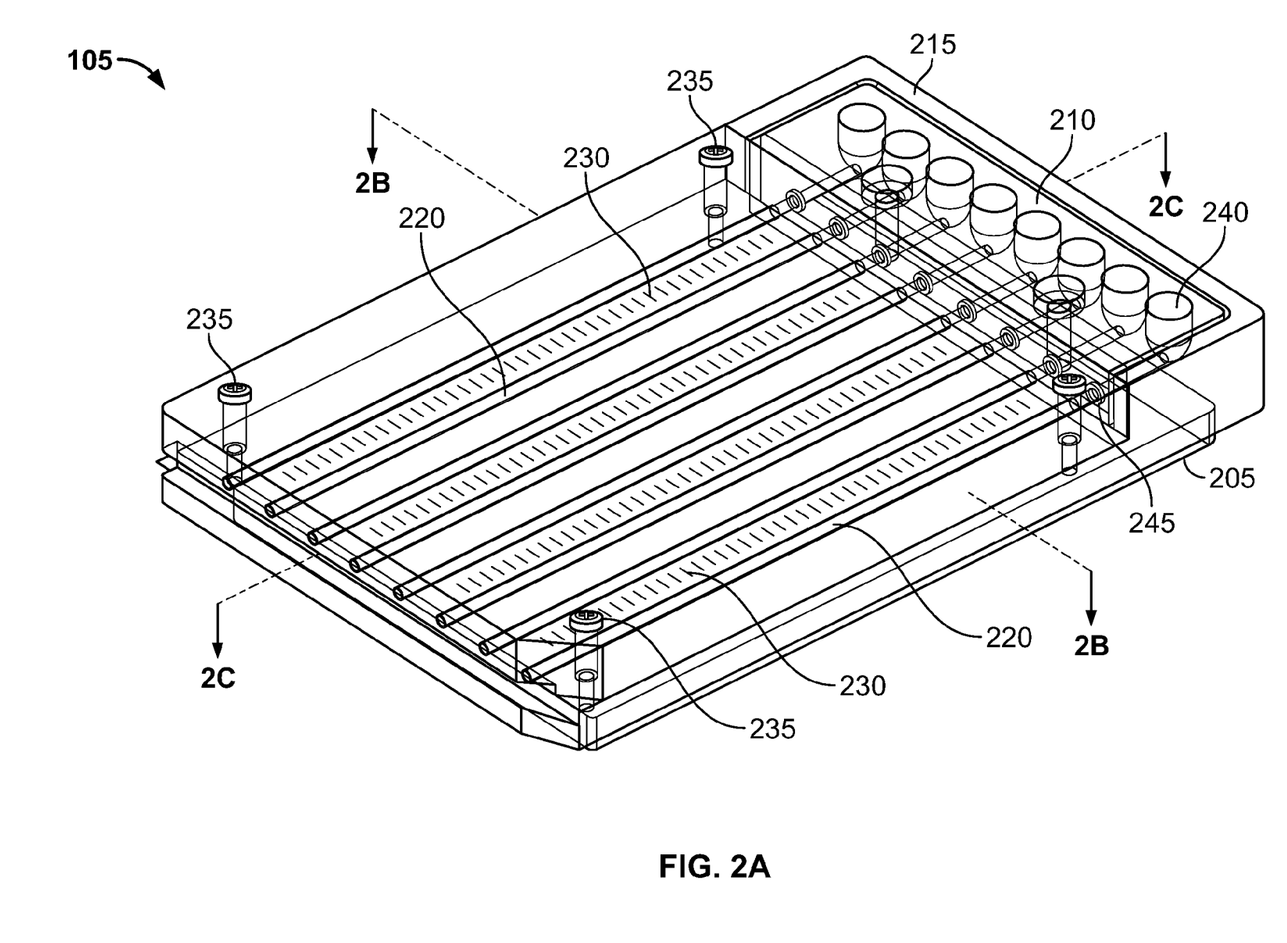
FIG. 2A shows a perspective, transparent view of the volume dispense verification device.
Figure 2B:
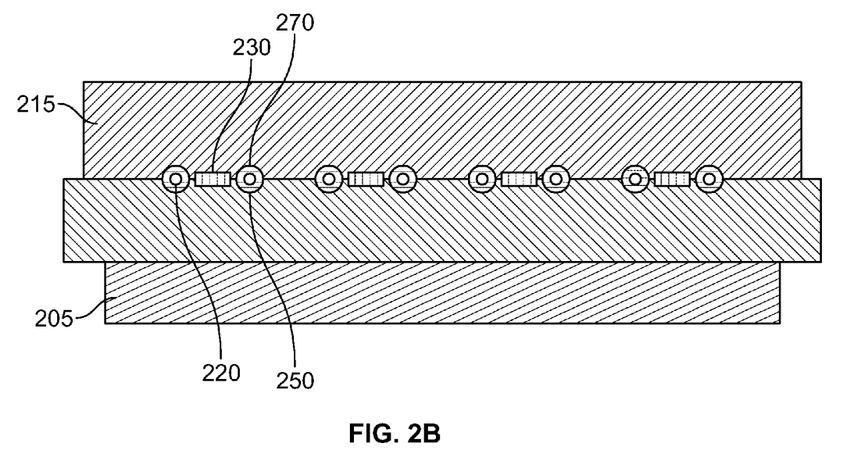
FIG. 2B shows a cross-sectional view of the device taken along lines B-B of FIG. 2A.
Figure 2C:
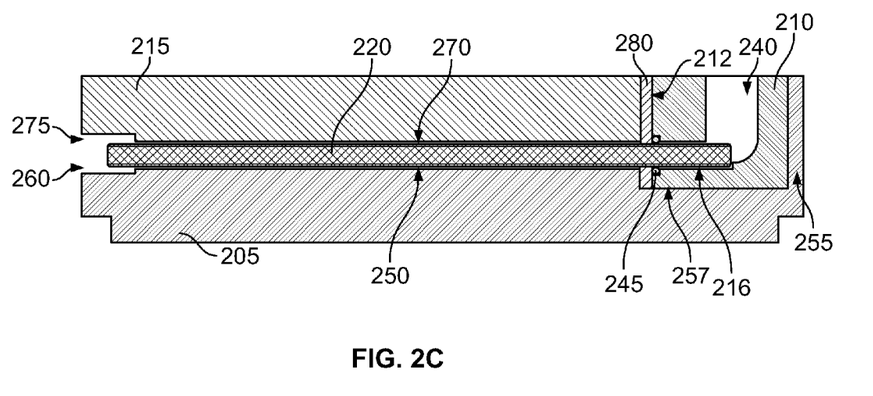
FIG. 2C shows a cross-sectional view of the device taken along lines C-C of FIG. 2A.

As shown in FIGS. 2A, 2B and 2C, in an exemplary embodiment the device 105 generally includes a base 205, dispense block 210, dispense block cover 280, cover 215, at least one capillary tube 220, at least 1 seal 245, and at least one metering element 230. The capillary tubes 220 and metering elements 230 are sandwiched between the base 205 on the underneath surface and the cover 215 on the upper surface. The dispense block 210 has wells 240 that are each connected to a respective capillary tube 220, the tubes 220 extending longitudinally across the base 205. The figures show the device having a plurality of capillary tubes coupled to a plurality of wells, although it should be appreciated that the device could include only a single capillary tube and a single well or a plurality of wells attached to a single capillary tube.

Figure 3:
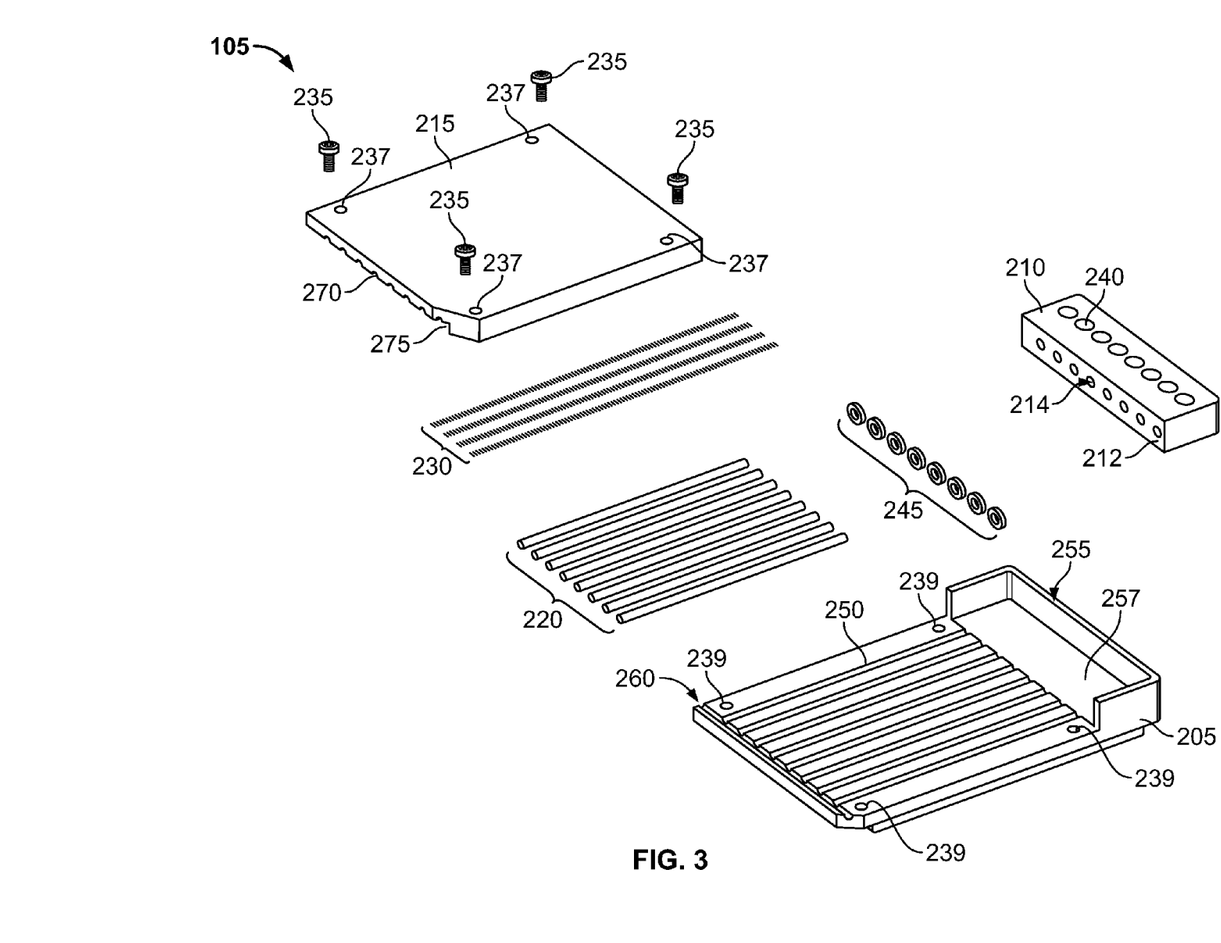
FIG. 3 shows an exploded view of the device of FIG. 2.

The base 205 can be inserted into standard sample carriers of known microtiter plate devices, including automated workstations. As best shown in FIGS. 2C and 3, in an exemplary embodiment the upper surface of the base 205 has at one end a rectangular, shallow recess 257 surrounded on three sides by a raised portion 255. The upper surface of the base 205 also has evenly distributed longitudinal channels 250. The channels 250 extend from the recess 257 on one end to a groove 260 at the opposite end of the base 205. The groove 260 lies perpendicular to the channels 250. The base 205 acts as a support structure in that it supports and provides a surface for the metering elements 230 and capillary tubes 220 to be positioned. The structure shown in the figures is merely exemplary and can be varied. For example, the recess 257 need not be rectangular and the channels do not have to be evenly distributed.

As shown in FIGS. 2A, 2C, 3 and 4, the exemplary embodiment of the dispense block 210 has one or more dispense wells 240 in its upper surface. In one embodiment, the wells 240 are dimensioned and spaced according to wells of known standardized microtiter plates, for example the 8×12 or 96-well Nunc™ microtiter plates, although the wells 240 can be dimensioned and spaced in other manners. When the dispense block 210 is positioned in the recess 257 of the base 205, the wells 240 can receive fluid, for example, from a pipette 130 of an automated workstation 100. In the exemplary embodiment, the column of wells 240 is arranged in the standardized configuration as wells of microtiter plates known in the art, so that the device 105 is universal with any fluid handling machine that accepts microtiter plates known in the art. However, the arrangement of the wells can be varied. The dispense wells 240 have an intake 216 drilled at or near the bottom of the wells 240.

Figure 4:
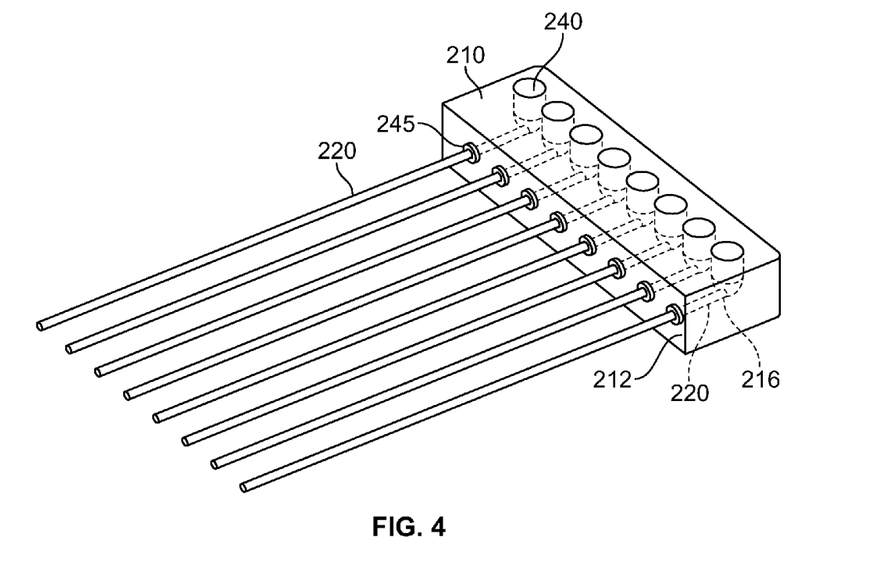
FIG. 4 shows a detailed view of the capillary block of the device of FIG. 2.
Figure 5:
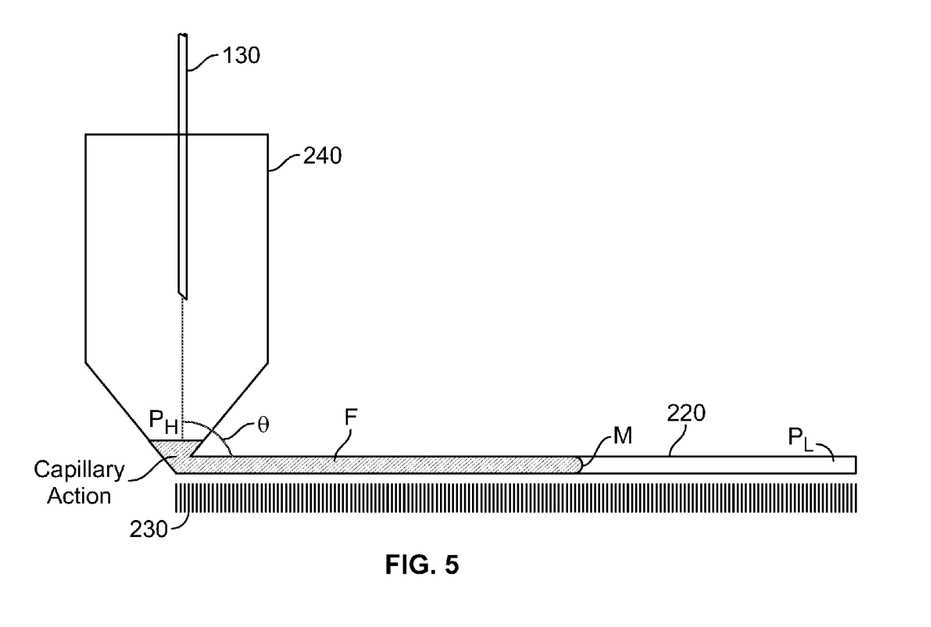
FIG. 5 shows a conceptual diagram of the device of FIG. 2.

The dispense block 210 also has one or more openings or holes that receive the capillary tubes 220 such that the capillary tubes enter the dispense block 210 and couple to the intake 216 of the dispense wells 240. Thus, the capillary tubes 220 and dispense wells 240 are in fluid communication with one another at intake 216. As best shown in FIG. 4, in the exemplary embodiment eight capillary tubes 220 connect to their respective dispense wells 240 at intake 216 at or near the bottom of the well 240. In one embodiment, as shown in FIG. 5, the angle θ between the dispense wells 240 and the capillary tubes 220 near the region of the intake 216 can be about 90 degrees from vertical. In other embodiments, the angle θ between the dispense wells 240 and the capillary tubes 220 near the region of the intake 216 can be about 85 degrees, about 80 degrees, about 75 degrees, about 70 degrees, about 65 degrees, about 60 degrees, about 55 degrees, about 50 degrees, about 45 degrees, or between about 0 degrees and about 90 degrees from vertical. The shape of the dispense wells can vary. In one embodiment, the dispense wells 240 have hemispherical bottoms and can include v-shape, u-shape or other round well bottoms. The round-shaped well bottom is conducive to the complete transfer of fluid inside the well 240 into the capillary tube 220. Round bottom wells avoid residual fluid volume collecting inside the well, which can occur, for example, with flat-bottomed wells.

With respect to FIGS. 2A and 2C, the dispense block 210 is positioned in the recess 257 of the base 205. The upper surface of the dispense block 210 can lie flush with the upper surface of the three walls of the raised portion 255. When the dispense block 210 is positioned in the recess 257, the capillary passages 214 align with the channels 250 of the base 205 and with channels 270 of the cover 215, as described in more detail below. The longitudinal channels 250 and 270 provide a surface in which the portion of the capillary tubes 220 extending beyond the dispense block 210 can reside. The majority of each capillary tube 220 can reside within the channels 250 and 270 of the base 205 and cover 215 and a smaller segment of each capillary tube 220 can reside inside the dispense block 210.

As best shown in FIG. 4, the capillary passages 214 are surrounded by seal members 245, such as O-rings or the like. The capillary passages 214 can be counter-bored such that the seal members 245 are positioned inside counter-bores within the wall 212 of the dispense block 210. In one embodiment, the seal members 245 are slightly compressed by the dispense block cover 280 (best shown in FIG. 2C) such that compression forces generate a seal around each capillary tube 220. The seal members 245 increase the likelihood that all of the fluid from each well 240 enters its respective capillary tube 220 and prevent leakage of fluid around the capillary tube 220. The seal members 245 also greatly reduce the elasticity of the fluid slug within the capillary tube 220, which can make accurate readings difficult. Similarly, generation of air bubbles inside the capillary tubes 220 is reduced by the presence of the seal members 245.

With respect to FIGS. 2A, 2B, 2C and 3, the cover 215 sits on top of the device 105 such that one end of the cover 215 abuts the raised portion 255 of the base 205 as well as the dispense block cover 280. Similarly, the upper surface of the cover 215 can lie flush with the upper surfaces of the raised portion 255, the dispense block cover 280 and dispense block 210. On its lower surface, the cover 215 has a series of channels 270 that correspond to the channels 250 of the base 205. The channels 270 extend longitudinally from the end of the cover 215 that abuts the dispense block cover 280 to the opposite end where there runs a groove 275. The groove 275 corresponds to the groove 260 of the base 205 and can lie perpendicular to the channels 270.

The base 205 and cover 215 are attached to each other by fixation elements 235, such as screws, bolts, etc. The base 205 and cover 215 can also be attached by other fixation methods such as by using glue. In the case of screws or bolts, apertures 237 can extend through the cover 215 and apertures 239 can extend through the base 205. When the device 105 is assembled, apertures 237 align with apertures 239. Fixation elements 235 can be inserted through the aligned apertures 237, 239 fixing the cover 215 to the base 205. When the cover 215 and the base 205 are fixed to one another, they sandwich the capillary tubes 220 and metering elements 230. As best shown in FIG. 2B, the base 205 and cover 215 that sandwich the capillary tubes 220 can lie flush against one another by virtue of their longitudinal channels 250, 270. The channels 250, 270 correspond and align with one another forming longitudinal passageways through which the capillary tubes 220 can extend. As mentioned, the particular structure of the device assembly is merely exemplary and it can be varied.

As described above, the capillary tubes 220 and metering elements 230 are sandwiched between the cover 215 and the base 205 (shown in FIGS. 2A, 2B and 2C). The capillary tubes 220 reside within the longitudinal passageways formed by the channels 250, 270. The metering elements 230 are graduated scales that are used to measure the length of the fluid slug or the distance the fluid slug travels within the capillary tube 220. The metering element 230 can be positioned next to each capillary tube 220 or can be positioned next to every other capillary tube 220 such that a metering element 230 lies between a pair of capillary tubes 220, as shown in the Figures. Alternatively, the entire base 205 can be covered by a metering element 230. The perpendicular grooves 260, 275 that align at one end of the device 105 prevent the wicking of fluid by the metering elements 230 from the end of the capillary tube 220 that could potentially occur.

In use, fluid is dispensed into one or more of the wells 240. The fluid passes through the intake and into a respective capillary tube 220. FIG. 5 shows a conceptual diagram of the device 105. The movement of the fluid from the well 240 into the capillary tube 220 is governed by the capillary force equation. The height h of a liquid column is governed by:

$$h = \frac{2T * \cos \theta}{\rho g r}$$

where
T=surface tension (J/m$^2$ or N/m)
$\theta$=contact angle
$\rho$=density of fluid (kg/m$^3$)
g=acceleration due to gravity (m/s$^2$)
r=radius of tube (m)

Capillary movement occurs when the adhesive intermolecular forces between the fluid and the tube 220 are stronger than the cohesive intermolecular forces within the fluid. Surface tension pulls a fluid column into the capillary tube 220 until there is a sufficient weight of fluid for gravitational forces to overcome the intermolecular forces. The weight of the fluid column is proportional to the square of the tube's diameter, but the contact area between the fluid and the tube is proportional only to the diameter of the capillary tube 220. Thus, a narrow tube will draw a fluid column further than a wide tube. Capillary tubes 220 used in the disclosed device 105 can include, for example, 90 µL capillary micropipets (#1-000-0900; Drummond Scientific Co., Broomall, Pa.). Increasing the contact angle causes the distance that the fluid travels in the capillary tube 220 to decrease. Setting the contact angle to horizontal or zero maximizes the distance that the fluid can travel in the capillary tube 220.

In the disclosed system, there is also a pressure differential between the fluid in the dispense well 240 and the air in the capillary tube 220 that also contributes to the flow of fluid into the capillary tube 220. In the dispense well 240, the weight of the fluid near the top causes pressure on the fluid near the bottom of the well 240 to increase. The region of higher pressure ($P_H$) near the bottom of the well 240 forces the fluid to flow toward the region of lower pressure ($P_L$) inside the capillary tube 220. At some point, all forces acting to pull fluid F into the capillary tube 220 equalizes and the flow stops. At this point, the meniscus M can be measured against a graduated scale or metering element 230 to determine how far the fluid moved. The distance the fluid traveled in the capillary tube 220 is a direct measure of the volume of the fluid.

Prior to use of the device 105, calibration curves can be generated for each channel of the device 105. This can be done by hand pipetting a range of fluid volumes into each well 240 of the device 105 and measuring the length of the fluid slugs against the metering elements 230. By plotting the known volumes from the pipettor versus the number of graduated lines from the metering element 230, a linear equation can be developed for each channel of the device 105 in order to correlate the graduations on the metering element 230 to volume.

To verify the accuracy and precision of volumes dispensed by, for example, automated workstations, the user places the device 105 onto a sample carrier of an automated workstation 100 and a dispense verification test is run. The device 105 can be evacuated by blowing canned air into the wells such that all residual moisture is removed. Service software can be used to run the test or the test can be run manually. A volume of reagent is aspirated and dispensed, such as by an instrument robot 110, into one or more of the dispense wells 240. A variety of dispense methods can be used. For example, the single aliquot method can be used where one aliquot of fluid is aspirated and then dispensed into each well. Alternatively, a multiple dispense method can be used where a larger volume of fluid is aspirated and then one aliquot dispensed into multiple wells. Fluid dispensed into the wells 240 is transferred from the well 240 into the capillary tube 220 by capillary action. The fluid travels some distance in the capillary tube 220 and then stops. At this point, the user can read the position of the meniscus M of the fluid with respect to the metering elements 230.

The readings can be performed manually or by using automated visualization techniques known in the art. One or more parts of the device 105 can be made of transparent or translucent material to allow for more accurate readings. Calibration curve generation can be performed to correlate the measured distance traveled by the fluid within the capillary tube 220 of the device 105 to an actual volume of fluid dispensed. Once a calibration curve is generated, the distance that the fluid travels into the capillary tube (as measured relative to the metering elements 230) is used as a measure of the volume of fluid that was dispensed into the well. The conversion from the distance traveled to volume can be performed manually using the calibration curve or it can be performed automatically using a computer into which the calibration curve has been entered. In one embodiment, the calibration is performed and the metering element 230 is configured such that it displays a scale of fluid volumes rather than distance of the fluid into the capillary tube. Calibration curves can be generated for each capillary tube 220 such as described in Example 1.

Surface tension, viscosity, density and temperature of the fluid can lead to different dispensed volumes. For example, the addition of a solute (buffer, preservative, protein or chromagen) to the fluid can lower the surface tension and increase the dispensed volume. Therefore, a calibration curve can be created for each fluid type to be dispensed. Further, the configuration of the capillary tubes 220 with the dispense wells 240 can also be adjusted for fluids of varying surface tensions. For example, for fluids with slightly lower surface tension the capillary tubes 220 can be inserted further into the dispense wells 240 at intake 216 to restrict flow. For fluids with slightly higher surface tension, the capillary tubes 220 can be pulled further away from the intake 216 to allow more flow.

The range of fluid volumes that can be verified using the disclosed device 105 includes, for example, volumes between approximately 10 μl and 100 μL, more specifically, volumes between approximately 20 μl and 90 μl and even more specifically, volumes between approximately 25 μl and 85 μl. Volumes can be verified to less than about 1 μL precision and to an accuracy of about ±1 L between about 30 μL and 65 μL; ±3 μL between about 15 μL and 30 μL; +2/−1 μL between about 65 μL and 70 μL.

The following examples are included for illustrative purposes only and are not intended to limit the scope of the claims.

EXAMPLES

Example 1

Calibration Curve Generation

Calibration curves are generated for individual capillary tubes of the disclosed volume verification device. A 2% ethanol solution is pipetted into each dispense well using fluid volumes ranging between 20 μL to 80 μL. The number of marks on the graduated metering element to the meniscus of the fluid in the capillary tubes are counted, such as by manual methods. Table 1 shows the number of marks to the meniscus for each capillary tube (tubes 1-8) at each volume dispensed (20 μL, 30 μL, 40 μL, 50 μL, 60 μL, 70 μL and 80 μL). The data are plotted and fit to linear equations to convert distance the fluid moved in the capillary tubes to volume of fluid dispensed into the wells.

TABLE 1

Calibration curve data using 2% EtOH solution

| | 20 | 30 | 40 | 50 | 60 | 70 | 80 | slope | y-int |
|---|---|---|---|---|---|---|---|---|---|
| 1 | 6 | 14.5 | 20.5 | 30.5 | 39 | 48.5 | 52 | 0.80 | −9.95 |
| 2 | 6 | 13 | 21.5 | 30 | 38.5 | 46 | 54 | 0.81 | −10.68 |
| 3 | 5 | 14.5 | 23 | 31 | 38 | 45 | 56.5 | 0.82 | −10.73 |
| 4 | 4 | 14.5 | 19.5 | 31 | 38 | 46 | 54 | 0.83 | −11.77 |
| 5 | 7 | 13.5 | 21.5 | 30.5 | 39 | 49 | 54 | 0.82 | −10.34 |
| 6 | 6 | 15.5 | 23.5 | 31.5 | 37 | 45 | 54.5 | 0.78 | −8.50 |
| 7 | 6.5 | 14.5 | 22.5 | 30.5 | 36 | 45.5 | 53 | 0.77 | −8.61 |
| 8 | 6 | 14 | 20.5 | 31.5 | 40.5 | 47 | 57.5 | 0.86 | −11.95 |

Example 2

Comparison of Volume Verification Device to Gravimetric Volume Verification Methods Volumes measured using the disclosed volume verification device are compared to gravimetric techniques. Fifty μL of 2% EtOH is pipetted into each of the 8 wells of the volume verification device using a Gilson Rainin P200 Pipetman (Table 2) or an automated fluid handling instrument NC400 (Table 4). The fluid volumes are measured using the calibration curves generated by the method described in Example 1. Subsequently, 50 μL aliquots of 2% EtOH is dispensed using an automated fluid handling instrument (NC400, Nanogen, Inc.) onto a Mettler Toledo PB3002 Balance and a Mettler Toledo AT200 Balance (Table 3). The results indicated that the disclosed volume verification device measures to a precision of 0.5 μL whereas the Mettler Toledo AT200 precision balance measures to a precision of 0.1 mg or 0.1 μL. The Mettler Toledo PB3002 balance is not adequate to measure at this volume.

Comparing the coefficient of variance (% cv) when volumes are dispensed using the automated fluid handling instrument shows nearly equivalent results between the AT200 balance and the disclosed device. The AT200% cv is 1.89% while the average of all channels on the disclosed device is 2.00%. The % cv measured when the device is loaded manually with the pipettor is found to average 3.97%. This indicates that a manual pipettor is less precise than the automated NC400 syringe pump and robot. This data also indicates that the error measured in the disclosed device and the AT200 balance are nearly the same and that the bulk of the error is most probably due to the NC400 syringe pump and robot.

TABLE 2

Volumes read on device when loaded by hand using Gilson P200 Pipetman

| Channel | 1 | 2 | 3 | 4 | 5 | avg | sd | % cv | range |
|---|---|---|---|---|---|---|---|---|---|
| 1 | 48.6 | 49.8 | 51.1 | 52.3 | 51.7 | 50.69 | 1.50 | 2.96% | 3.7 |
| 2 | 50.2 | 50.2 | 50.2 | 49.6 | 50.8 | 50.18 | 0.44 | 0.87% | 1.2 |
| 3 | 52.5 | 51.9 | 51.3 | 48.3 | 49.5 | 50.69 | 1.77 | 3.49% | 4.3 |
| 4 | 51.1 | 52.9 | 52.3 | 50.5 | 50.5 | 51.49 | 1.10 | 2.13% | 2.4 |
| 5 | 52.9 | 49.2 | 49.2 | 49.2 | 47.4 | 49.58 | 2.00 | 4.04% | 5.5 |
| 6 | 53.3 | 48.8 | 52.7 | 50.1 | 50.7 | 51.12 | 1.85 | 3.62% | 4.5 |
| 7 | 53.5 | 51.6 | 50.3 | 49.0 | 50.3 | 50.93 | 1.72 | 3.38% | 4.6 |
| 8 | 50.6 | 51.7 | 51.7 | 47.7 | 51.2 | 50.58 | 1.70 | 3.36% | 4.1 |

TABLE 3

Volumes read on Mettler Toledo balances when dispensed with NC400 Instrument 0110

| Mettler Toledo PB3002 (QA486) Calibrated October 2006 | | | | | Mettler Toledo AT200 (QA075) Calibrated February 2006 | | | | |
|---|---|---|---|---|---|---|---|---|---|
| Tube | Pre (g) | Post (g) | diff | uL | Tube | Pre (mg) | Post (mg) | diff | uL |
| 1 | 0.9 | 0.94 | 0.04 | 40 | 1 | 897.7 | 945.3 | 47.6 | 47.6 |
| 2 | 0.91 | 0.95 | 0.04 | 40 | 2 | 903.7 | 952.5 | 48.8 | 48.8 |
| 3 | 0.89 | 0.94 | 0.05 | 50 | 3 | 881.6 | 928.9 | 47.3 | 47.3 |
| 4 | 0.9 | 0.95 | 0.05 | 50 | 4 | 896 | 943 | 47 | 47 |
| 5 | 0.9 | 0.94 | 0.04 | 40 | 5 | 913.5 | 962.8 | 49.3 | 49.3 |
| 6 | 0.9 | 0.95 | 0.05 | 50 | 6 | 891.5 | 938.5 | 47 | 47 |
| 7 | 0.91 | 0.95 | 0.04 | 40 | 7 | 891.1 | 940.4 | 49.3 | 49.3 |
| 8 | 0.89 | 0.94 | 0.05 | 50 | 8 | 888.6 | 937.1 | 48.5 | 48.5 |
| 9 | 0.88 | 0.93 | 0.05 | 50 | 9 | 892.1 | 939.4 | 47.3 | 47.3 |
| 10 | 0.88 | 0.93 | 0.05 | 50 | 10 | 899.6 | 947.5 | 47.9 | 47.9 |
| | | | avg | 46 | | | | avg | 48 |
| | | | sd | 5.163978 | | | | sd | 0.907989 |
| | | | % cv | 11.23% | | | | % cv | 1.89% |
| | | | range | 10 | | | | range | 2.3 |

TABLE 4

Volumes read on device when dispensed with NC400 Instrument 0110
Oct. 20, 2006 Instrument delivered fluid (50 uL, H2O, Converted to uL using calibration curves)

| Channel | 1 | 2 | 3 | 4 | 5 | 6 | 7 | 8 | 9 | 10 | avg | sd | % cv | range |
|---|---|---|---|---|---|---|---|---|---|---|---|---|---|---|
| 1 | 48.6 | 49.8 | 49.2 | 49.2 | 49.2 | 49.2 | 49.2 | 49.2 | 49.2 | 49.2 | 49.20 | 0.29 | 0.60% | 1.2 |
| 2 | 49.6 | 49.6 | 49.6 | 49.6 | 49.6 | 49.6 | 49.6 | 51.4 | 50.8 | 49.6 | 49.87 | 0.67 | 1.34% | 1.9 |
| 3 | 48.9 | 48.9 | 49.5 | 49.5 | 50.7 | 48.9 | 48.9 | 50.1 | 49.5 | 49.5 | 49.42 | 0.60 | 1.22% | 1.8 |
| 4 | 52.3 | 50.5 | 50.5 | 52.9 | 52.9 | 50.5 | 52.3 | 50.5 | 50.5 | 52.9 | 51.61 | 1.17 | 2.26% | 2.4 |
| 5 | 48.6 | 49.2 | 51.7 | 49.2 | 51.7 | 51.7 | 51.0 | 49.2 | 49.2 | 51.7 | 50.32 | 1.31 | 2.61% | 3.1 |
| 6 | 52.0 | 52.7 | 52.7 | 50.1 | 52.0 | 52.7 | 50.1 | 50.1 | 52.7 | 50.1 | 51.50 | 1.24 | 2.41% | 2.6 |
| 7 | 51.6 | 51.6 | 49.0 | 49.0 | 52.9 | 52.2 | 49.6 | 52.9 | 49.6 | 51.6 | 50.99 | 1.55 | 3.04% | 3.9 |
| 8 | 50.6 | 49.4 | 48.8 | 48.3 | 48.8 | 51.7 | 48.3 | 48.8 | 47.7 | 48.3 | 49.07 | 1.23 | 2.51% | 4.1 |

Example 3

Determination of the Dynamic Range of the Volume Dispense Verification Device

Figure 6:
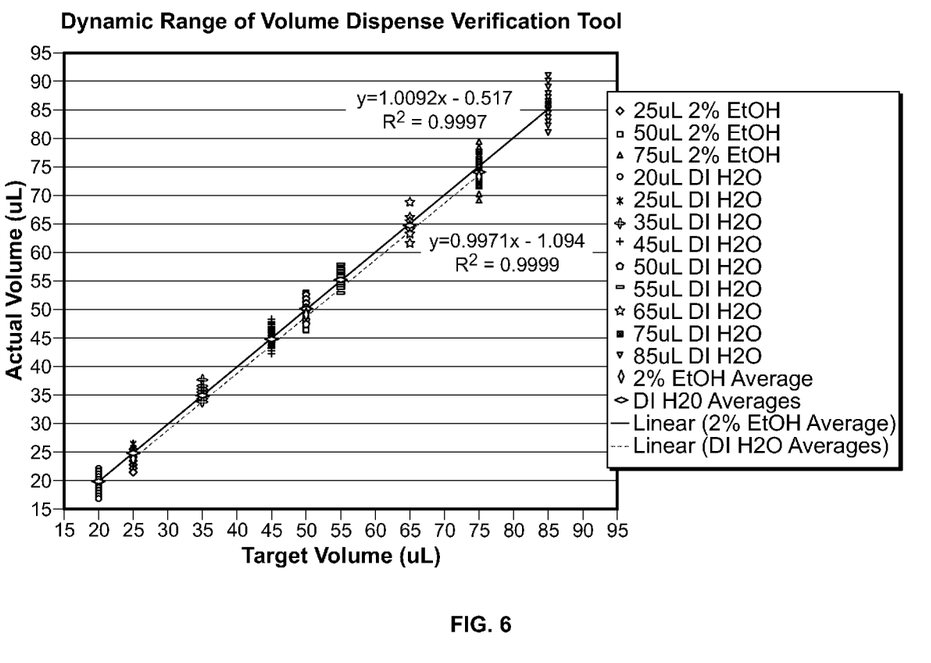
FIG. 6 shows an exemplary dynamic range of volumes determined by the device of FIG. 2.

To determine the dynamic range of the disclosed device, varying dispense volumes of either deionized water (DI H$_2$O) or 2% ethanol (ETOH) solution are loaded into each of the eight wells using the NC400 automated fluid handling instrument. FIG. 6 shows the volumes determined by the device as having an optimum usable range between 20 μL to 85 μL. At smaller volumes, fluid can stick to the walls of the dispense well and are not drawn into the capillary tube. Lightly tapping the device shifts the fluid into contact with the capillary tube such that the fluid will flow into the device.

Figure 7:
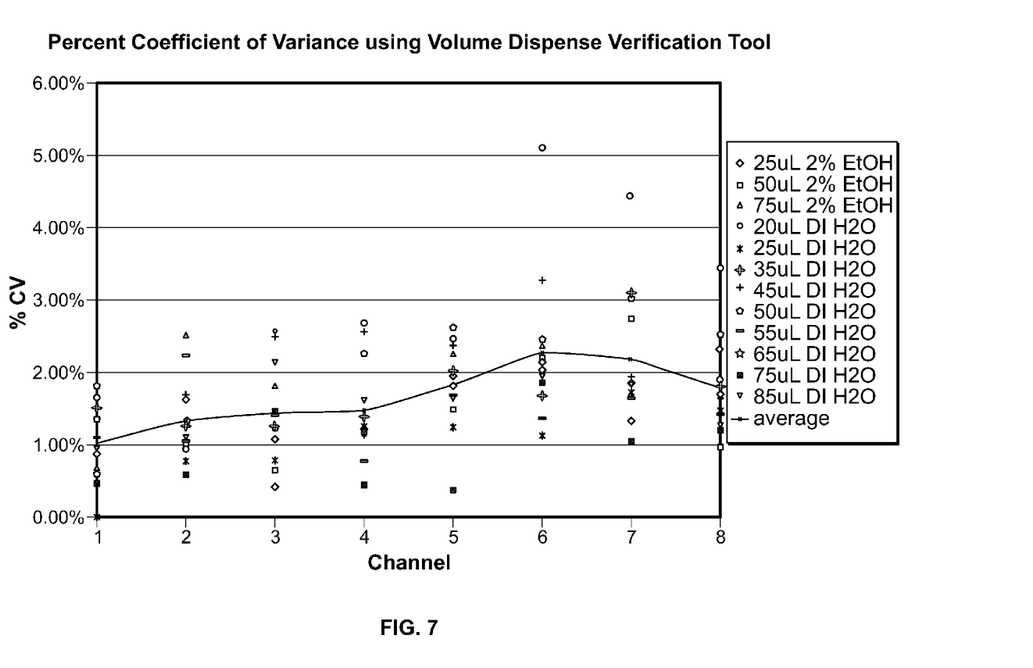
FIG. 7 shows an exemplary percent coefficient of variance for the device of FIG. 2.

FIG. 7 shows the percent coefficient of variance (% cv) for each channel of the device. The data indicate that the % cv could have been improved for channels 5-8 lowering the flow rate, such as by pushing the capillary tubes inward slightly.

Example 4

Volume Verification using Multi-dispensing Techniques

Figure 8:
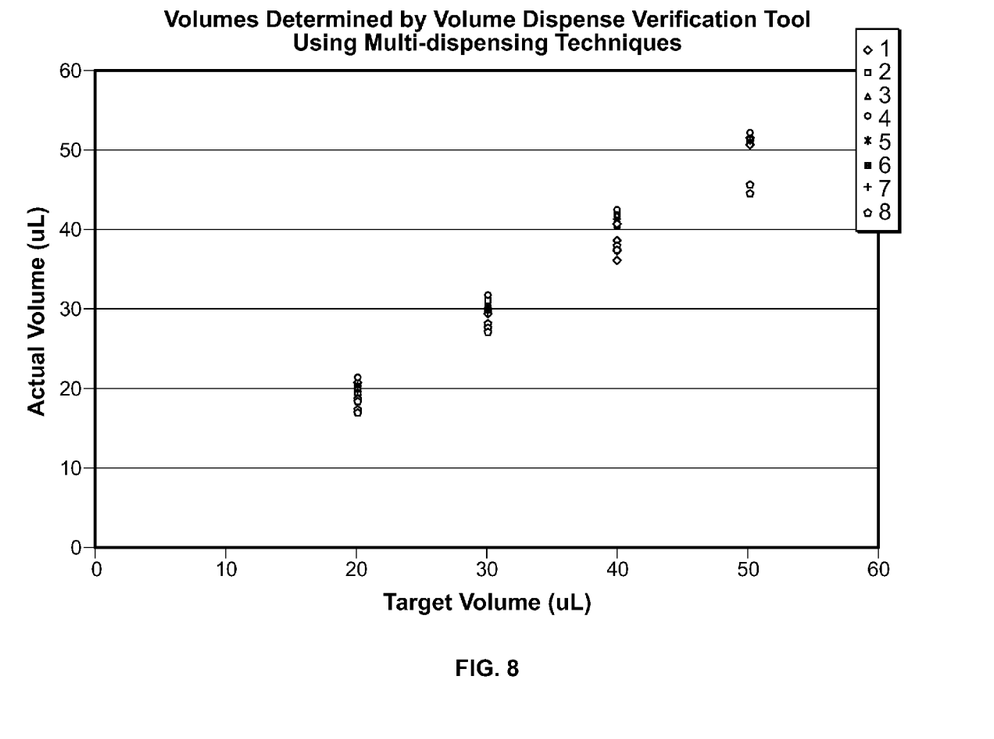
FIG. 8 shows exemplary volumes determined by the device of FIG. 2 using multi-dispensing techniques with an automated fluid handling instrument.

One large volume is aspirated by a robotic pipette on an automated NC400 device and equal sized smaller aliquots are dispensed into the eight wells of the device (FIG. 8). FIG. 8 shows that the robotic pipette aspirated volumes of 160 μL, 240 μL, 320 μL, or 400 μL and dispensed into each of the eight channels aliquots of 20 μL, 30 μL, 40 μL, or 50 μL, respectively. Thus, fluid volume aspirated is equal to the dispense volume divided by eight. FIG. 8 shows that the final well dispensed (well 8) frequently measured a smaller volume than the target dispense volume. Thus, to insure a more accurate and consistent volume dispense for each well, the starting aspirated fluid volume should be slightly greater than the cumulative volume of the eight dispensed volumes.

Figure 9:
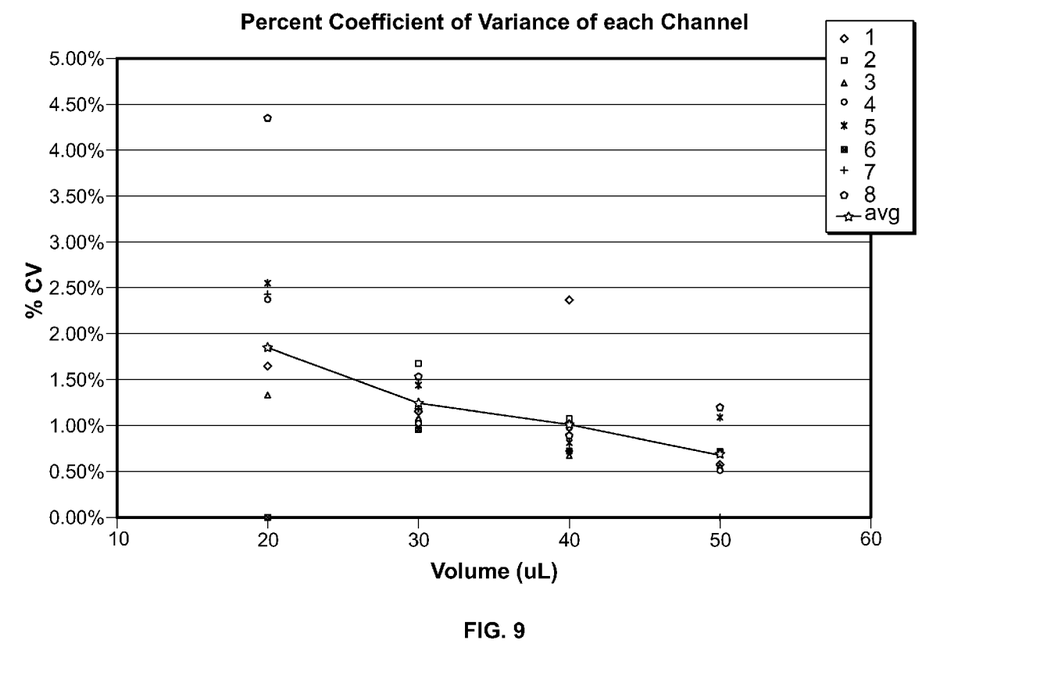
FIG. 9 shows exemplary percent coefficient of variant for each channel of the device of FIG. 2 using multi-dispensing techniques with an automated fluid handling instrument.

FIG. 9 shows that multi-dispensing lowers the % cvs which averages 1.19% and that the expected linear relationship of % cv decreases as volume increases. The data also provides further evidence that precision and accuracy of the device is equivalent to gravimetric methods using a precision balance (i.e. as low as 0.1 mg). When comparing single dispense to single dispense the % cvs are equivalent. Further, removing air gaps in the dispense system lowers % cvs.

Although embodiments of various devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed:

1. A device for measuring fluid dispense volumes, comprising one or more wells adapted to receive a fluid, each one of said one or more wells being fluidly coupled to a single tube having an internal passageway, said single tube being further coupled to a graduated scale, wherein
   fluid in each one of said one or more wells passes into said internal passageway via capillary action and travels a distance to form a fluid column having a meniscus spaced from the well, said meniscus having a location intermediate the ends of said tube; and
   the location of the meniscus measured against the graduated scale indicates the distance traveled by the fluid, said distance being a direct measure of the fluid volume in the well.

2. The device of claim 1, further comprising a support structure that supports the tube fluidly coupled to each one of the one or more wells.

3. The device of claim 2, wherein the support structure is removably received and secured in a sample carrier of a liquid handling system.

4. The device of claim 3, wherein the sample carrier is adapted to receive a standardized microtiter plate.

5. The device of claim 1, wherein the one or more wells are fluidly coupled to a dispensing passageway of a liquid handling system.

6. The device of claim 1, wherein at least one of the one or more wells has at least a partial spherical-shape.

7. The device of claim 1, wherein at least one of the one or more wells has a rounded shape.

8. The device of claim 1, wherein at least one of the one or more wells has a V-shape.

9. The device of claim 1, wherein the coupling between each one of said one or more wells and the tube coupled thereto forms an angle of at least about 90 degrees from vertical.

10. The device of claim 1, wherein the coupling between each one of said one or more wells and the tube coupled thereto forms an angle of at least about 85 degrees from vertical.

11. The device of claim 1, wherein the coupling between each one of said one or more wells and the tube coupled thereto forms an angle of at least about 80 degrees from vertical.

12. The device of claim 1, wherein the coupling between each one of said one or more wells and the tube coupled thereto forms an angle of between about 0 degrees and about 90 degrees from vertical.

13. The device of claim 1, further comprising (i) a support structure that supports the tube fluidly coupled to each one of the one or more wells; and (ii) a seal member that provides a seal between the tube and the support structure.

14. The device of claim 13, wherein the seal member is an o-ring.

* * * * *